US008768468B2

(12) United States Patent  (10) Patent No.: US 8,768,468 B2
Garcia et al.  (45) Date of Patent: Jul. 1, 2014

(54) DEVICE FOR NEURO-PHYSIOLOGIC STIMULATION

(71) Applicants: Julio Luis Garcia, Coral Gables, FL (US); Oresteban Carabeo, Miami Gardens, FL (US); Ruben Valdes, Beverly Hills, FL (US); Robert Valdes, Miami Lakes, FL (US)

(72) Inventors: Julio Luis Garcia, Coral Gables, FL (US); Oresteban Carabeo, Miami Gardens, FL (US); Ruben Valdes, Beverly Hills, FL (US); Robert Valdes, Miami Lakes, FL (US)

(73) Assignee: Mitosis, Inc., Sunrise, FL (US)

( * ) Notice: Subject to any disclaimer, the term of this patent is extended or adjusted under 35 U.S.C. 154(b) by 0 days.

(21) Appl. No.: 13/875,923

(22) Filed: May 2, 2013

(65) Prior Publication Data

US 2014/0121737 A1    May 1, 2014

Related U.S. Application Data

(63) Continuation-in-part of application No. 13/663,658, filed on Oct. 30, 2012, now Pat. No. 8,457,745, and a continuation-in-part of application No. 13/675,287, filed on Nov. 13, 2012.

(51) Int. Cl.
    *A61N 1/36* (2006.01)

(52) U.S. Cl.
    USPC .......................................................... 607/40

(58) Field of Classification Search
    USPC ............ 607/145–150, 133, 40, 46, 44, 45, 50
    See application file for complete search history.

(56) References Cited

U.S. PATENT DOCUMENTS

| 4,165,750 A | 8/1979 | Aleev et al. |
| 5,823,190 A | 10/1998 | Voipio |
| 8,078,281 B2 | 12/2011 | Priori et al. |

*Primary Examiner* — Carl H Layno
*Assistant Examiner* — Paula J Stice
(74) *Attorney, Agent, or Firm* — Melvin K. Silverman (57) ABSTRACT

An apparatus for the electro-physiologic stimulation of the human nervous system includes a positive electrical assembly having an integrated circuit (IC) producing a sequence of physiologically compatible and acceptable electromagnetic waveforms, the IC having ungrounded positive and negative outputs of the waveforms, a battery substantially in electrical communication with the IC board, a positive treatment pad at a bottom of the positive assembly in electrical communication with the positive output of the waveforms. An upper and middle housing is in swivel contact with a lower housing. Also included is a flexible housing for the electrical cable. Further included is a negative assembly in electrical communication with an opposite end of the cable, carrying the negative side of the waveforms, a negative treatment pad in axial electrical communication with a bottom of a housing secured about the cable.

11 Claims, 11 Drawing Sheets

DEVICE FOR NEURO-PHYSIOLOGIC STIMULATION

REFERENCE TO RELATED APPLICATION

This is a continuation-in-art of application Ser. No. 13/663,658, now U.S. Pat. No. 8,457,745, entitled Method, System and Apparatus for Control of Pancreatic Beta Cell Function to Improve Glucose Homeostatis and Insulin Production, filed Oct. 30, 2012, and of application Ser. No. 13/675,287, entitled Device for Neuro-Physiologic Stimulation, filed Nov. 12, 2012, and both are incorporated herein by reference in their entirety.

BACKGROUND OF THE INVENTION

With the exception of TENS machines, there exist very few bioelectrical systems that externally apply an electrical waveform, or a sequence thereof, to the human body. Yet less common are bioelectric systems that apply electrical waveforms to the human neurologic system. Some such systems are implanted into the human body, such as heart pacemakers.

U.S. Pat. No. 8,078,281 to Priori teaches a system of monitoring brain waves and providing a feedback for bio-stimulation of the brain.

U.S. Pat. No. 4,165,750 to Aleev teaches a system of electrical stimulation of muscles.

Electro-stimulation is sometimes used in diagnostic devices as in U.S. Pat. No. 5,823,190 to Voipio which is used in certain examinations of the human eye.

The present invention relates to an improvement of a special-purpose applicator of electrical waveforms directly to nerves of the sympathetic and parasympathetic nervous system, as disclosed in our pending Application Serial Numbers referenced above.

SUMMARY OF THE INVENTION

An apparatus for the electro-physiologic stimulation of the human nervous system includes (a) a positive electrical assembly having (i) an integrated circuit (IC) board or chip producing a sequence of physiologically compatible and acceptable electromagnetic waveforms, the IC board having outputs of ungrounded positive and negative waveforms; (ii) a battery in electrical communication with said IC board; (iii) a positive electrode treatment pad in electrical communication with said positive output of said waveforms, and securable within a complemental bottom of a upper housing; (iv) an upper housing in which said IC board is secured; and (v) a middle housing in axial rotational communication with said lower housing in which at least 90 degrees of rotation of the middle housing relative to said lower housing is enabled, said middle housing mechanically secured to said upper housing of the positive assembly. The apparatus also includes; an electrical cable having one end in electrical communication with said output of negative waveforms of said IC board. Further included is a negative electrical assembly having (i) a channel of a housing for receiving an opposite end of said cable, carrying said output of negative waveforms; (ii) a negative electrode treatment pad in selectable electrical communication with a bottom of said housing of said negative assembly; and (iii) an electrical coupling joining said end of said cable in said channel of said housing to said negative electrode treatment pad.

It is an object of the invention to provide an apparatus for the application of electro-neurologic waveforms to the anatomy of a patient.

It is a further object to provide an applicator for electro-neurologic waveforms to areas related to the vagus and celiac schema of the sympathetic nervous system.

It is another object to provide an apparatus useful in innervating neural pathways associated with the pancreas and the activity of its beta cells.

The above and yet other objects of the invention will become apparent from the hereinafter set forth Brief Description of the Drawings, Detailed Description of the invention and Claims appended herewith.

DETAILED DESCRIPTION OF THE INVENTION

Figure 1:
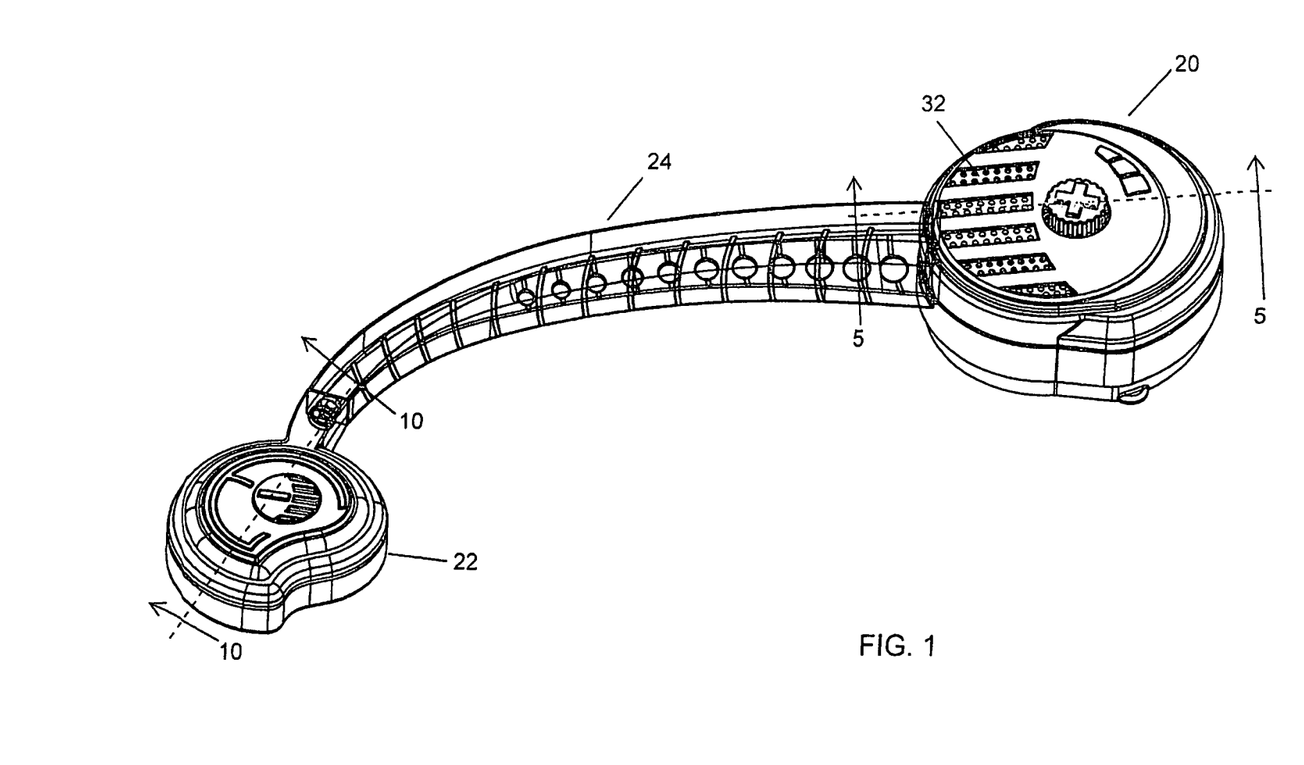
FIG. 1 is a top perspective view of the present apparatus.
Figure 2:
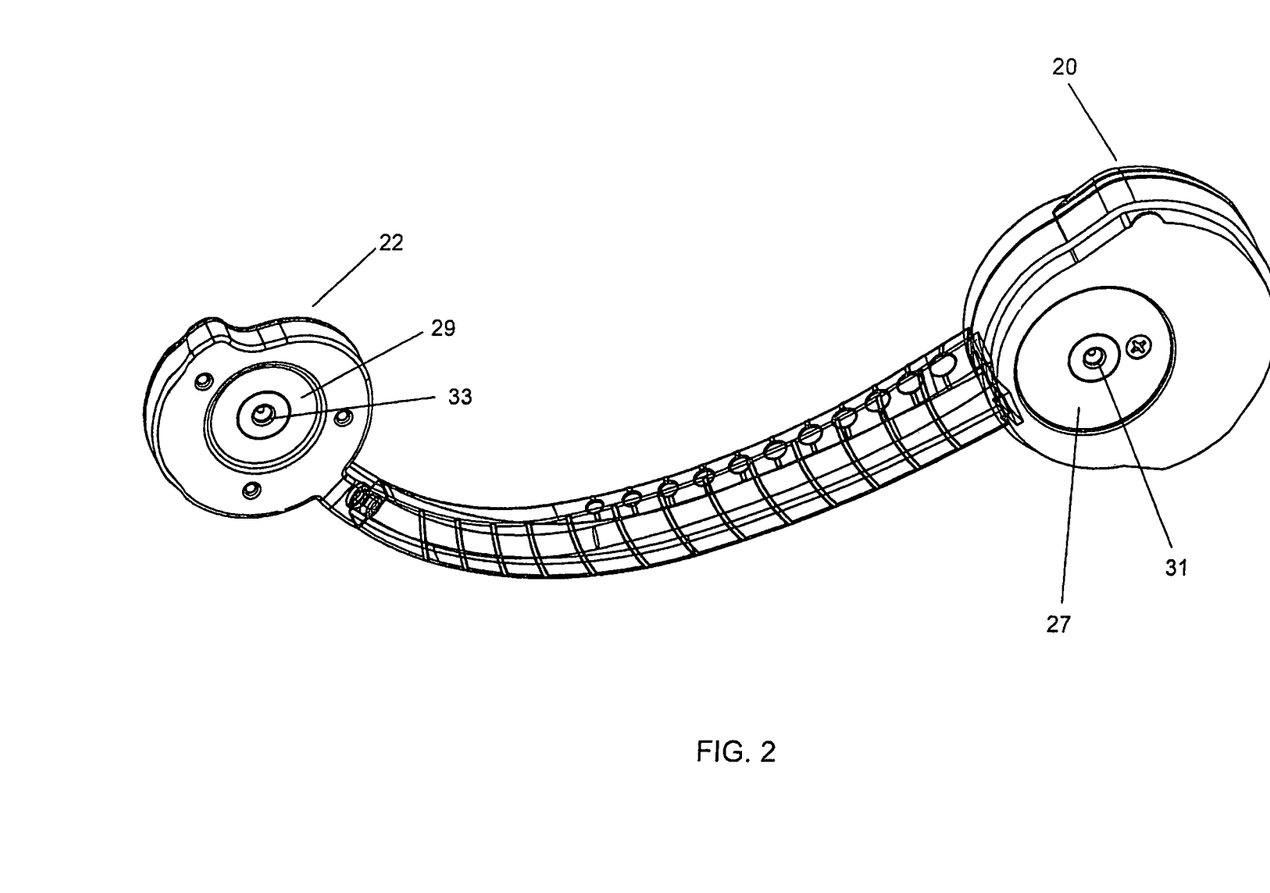
FIG. 2 is a bottom perspective view thereof.
Figure 3:
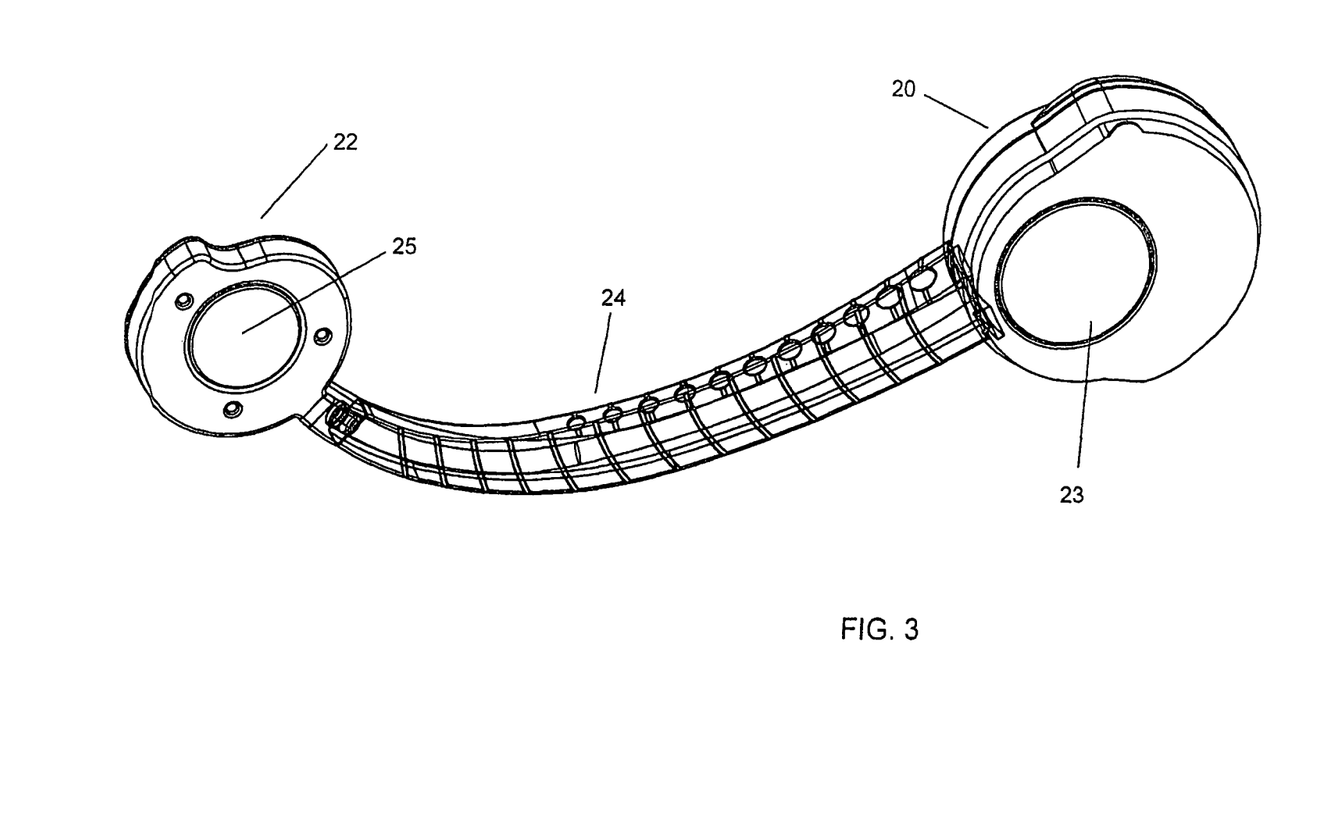
FIG. 3 is a view similar to FIG. 2 but with the treatment electrodes inserted thereinto.
Figure 4:
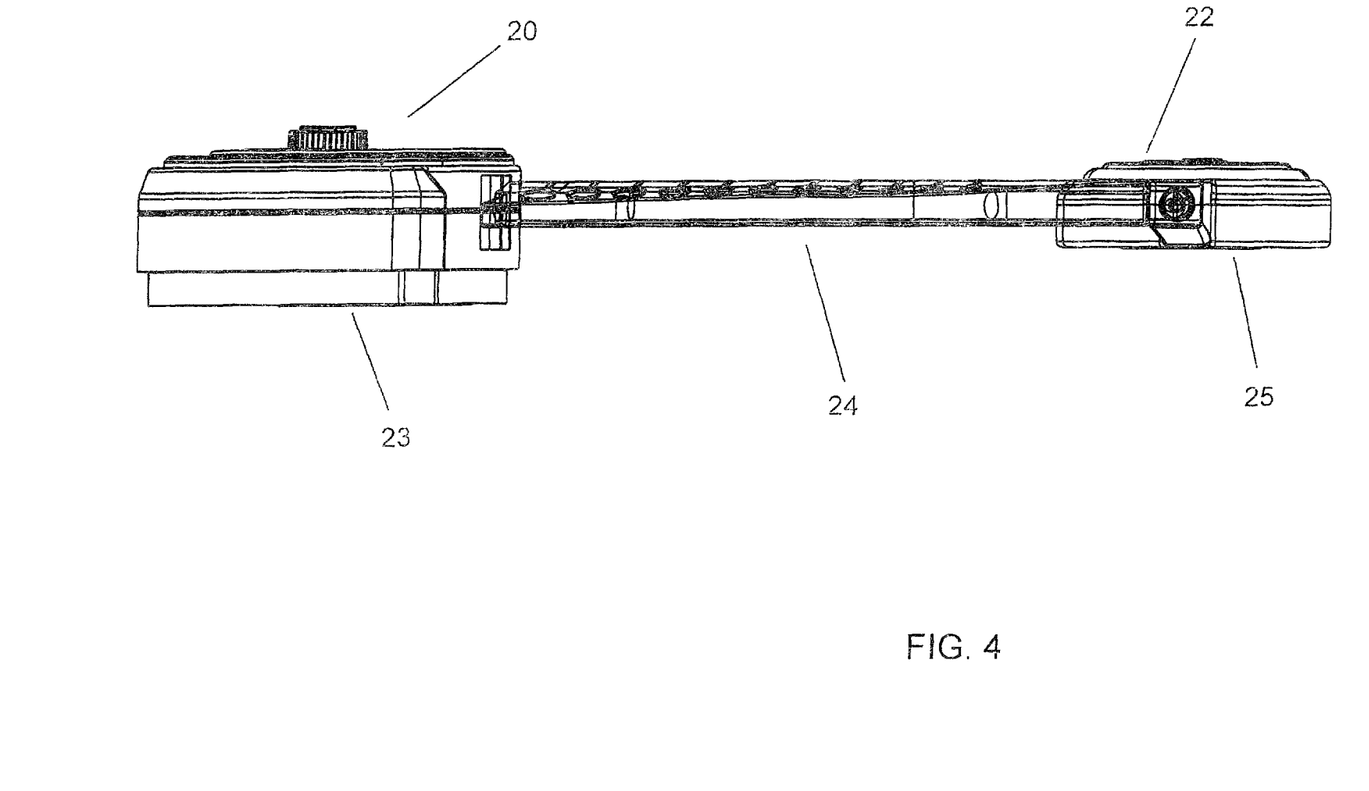
FIG. 4 is a front elevational view of the present apparatus.

With reference to FIGS. 1-4 there is shown the instant device for application of sequences of neurophysiologic electrical waveforms to the human body, A positive electrode assembly 20 and negative electrode assembly 22, connected by a flexible elongate cable housing 24 are shown in various views. Bottom views of the assemblies 20/22/24 are shown in FIGS. 2 and 3. Therein are also shown electrode pads 23 and 25.

As may be seen in FIG. 2, treatment pads 23 and 25 snap-fit into cavities 27 and 29 respectively of the bottom of the assemblies at threaded ports 31 and 33 respectively.

Figure 5:
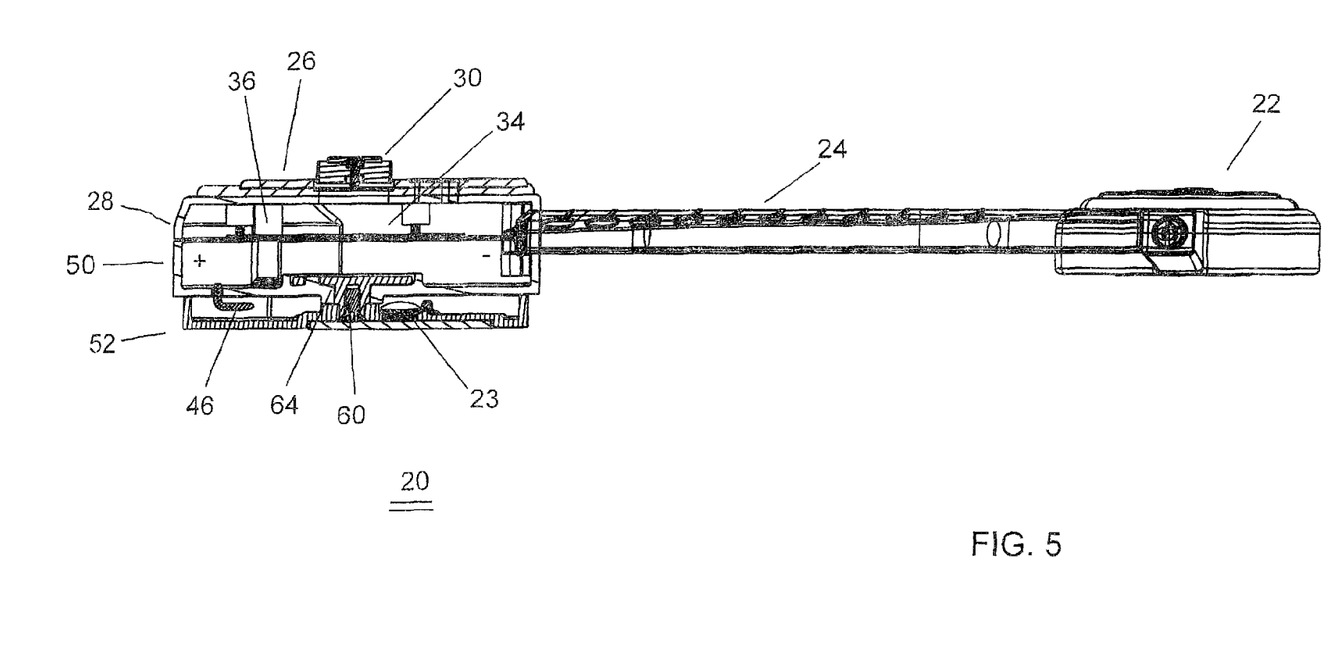
FIG. 5 is a cross-sectional view of the positive electrode assembly taken along Line 5-5 of FIG. 1.
Figure 6:
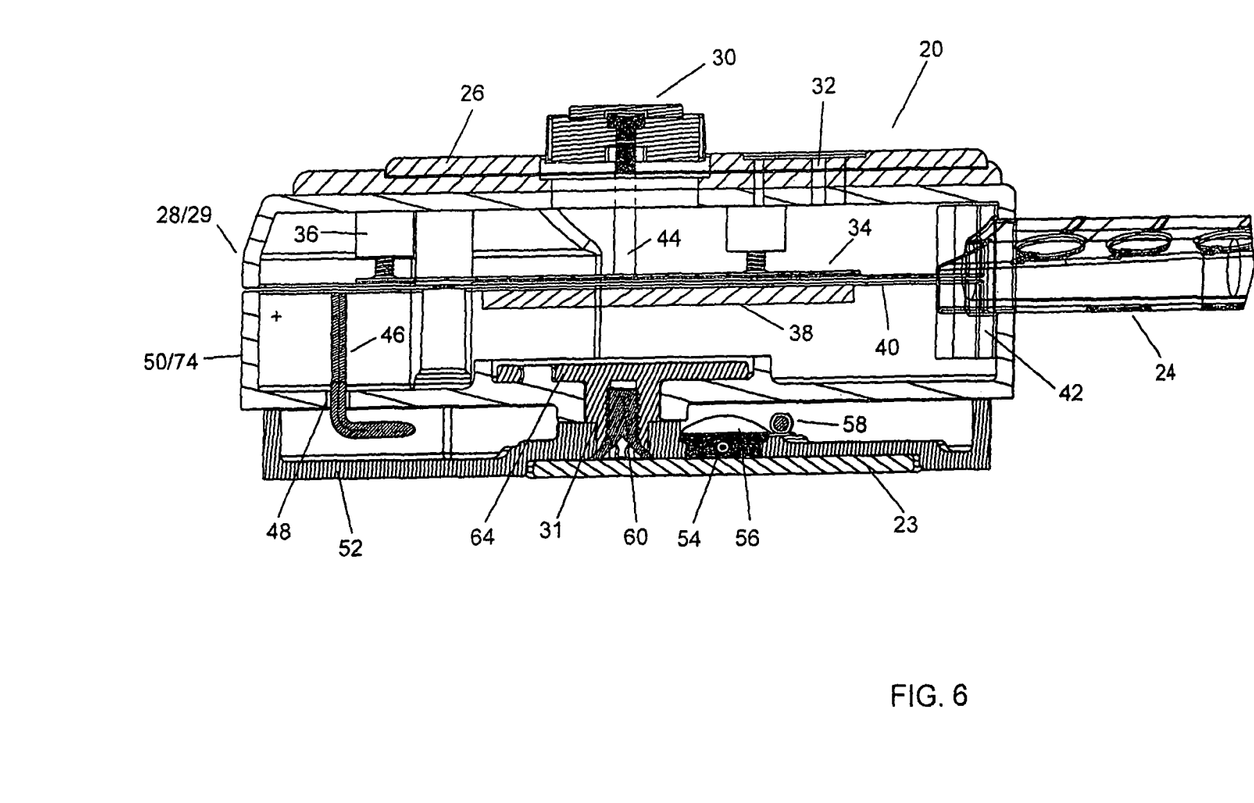
FIG. 6 is an enlarged view of the left hand side of FIG. 5.

Cross-sectional views taken through the middle of positive electrode assembly 20 through Line 5-5 of FIG. 1 are shown in FIGS. 5 and 6. Therein may be seen the general top 26 of upper housing 28 of the structure, and centrally disposed therein an on-off control 30 which also rotates to act as a potentiometer to control the voltage amplitude of the waveforms applied through the treatment pads 23/25. Said housing 28 includes vents 32 (see FIG. 6) and employs generally circular sidewalls 29. Upper housing 28 is offset from integrated circuit (IC) board 34 through the use of plastic members 36 which also stabilize the IC board relative to battery 38 (see FIG. 6) which may be a 3 VDC lithium battery. Further shown at the right of FIG. 6 is a flexible cable 40, held at a radial end by bracket 42, which cable is in electrical communication with the negative output side of the waveform produced by the IC board 34. Bracket 42 spans an interface between the upper and middle housing 50 and seats within notch 43. (See FIG. 7) and facilitates the rotation of negative assembly 22 relative to the positive assembly, as discussed below.

Figure 7:
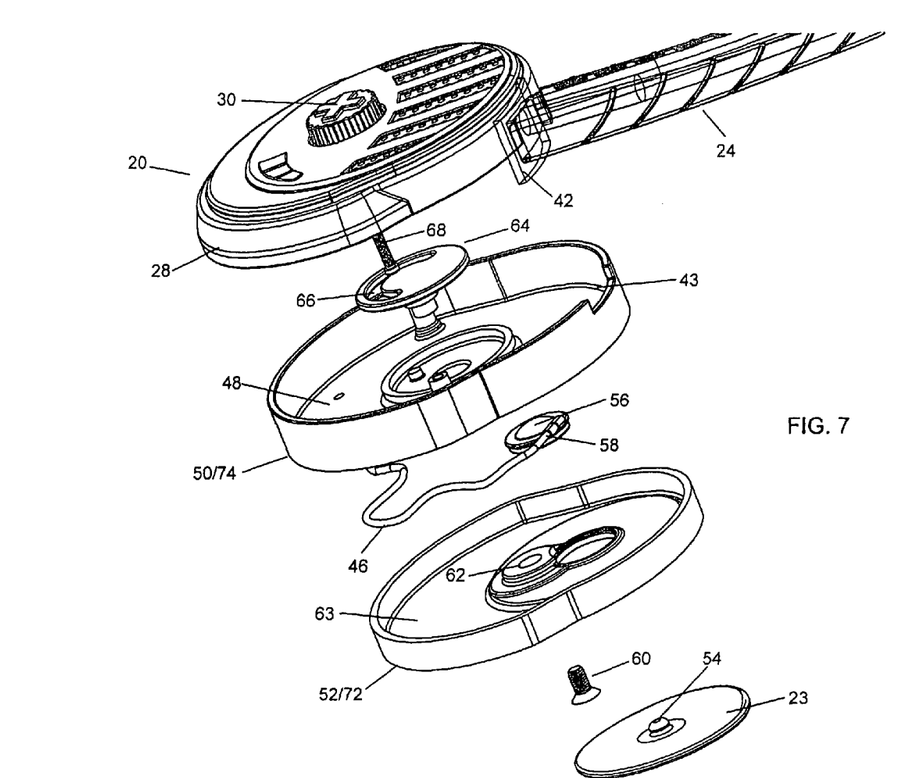
FIG. 7 is an exploded view showing the parts of the positive electrode assembly of FIG. 6.
Figure 8:
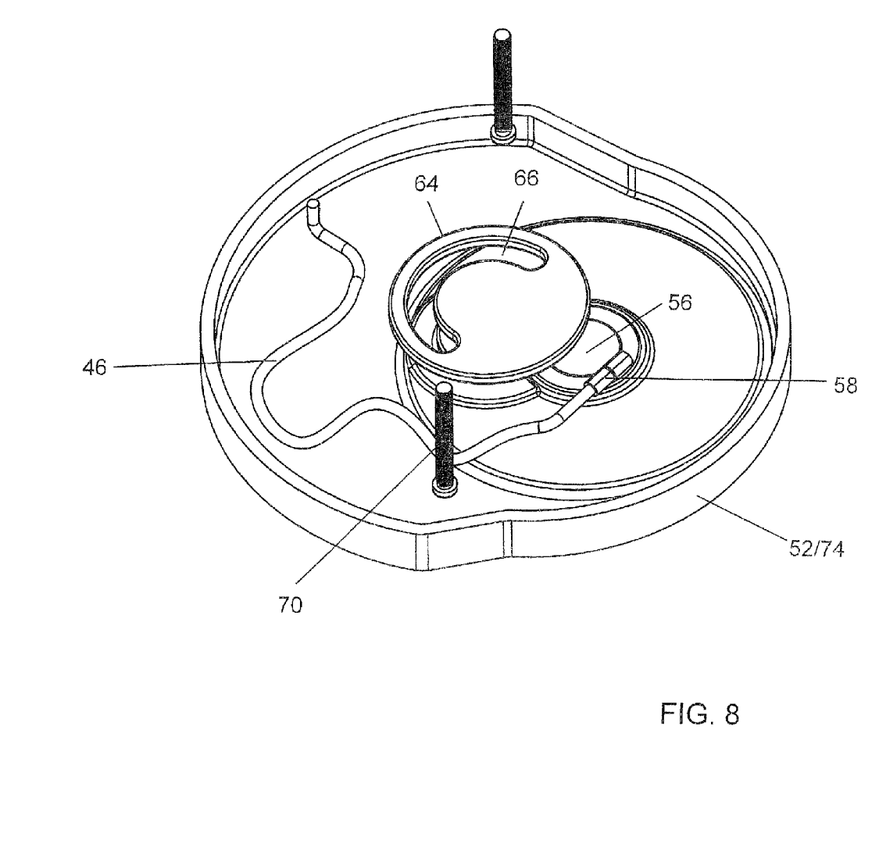
FIG. 8 is a perspective view of the lower housing of FIG. 7.
Figure 9:
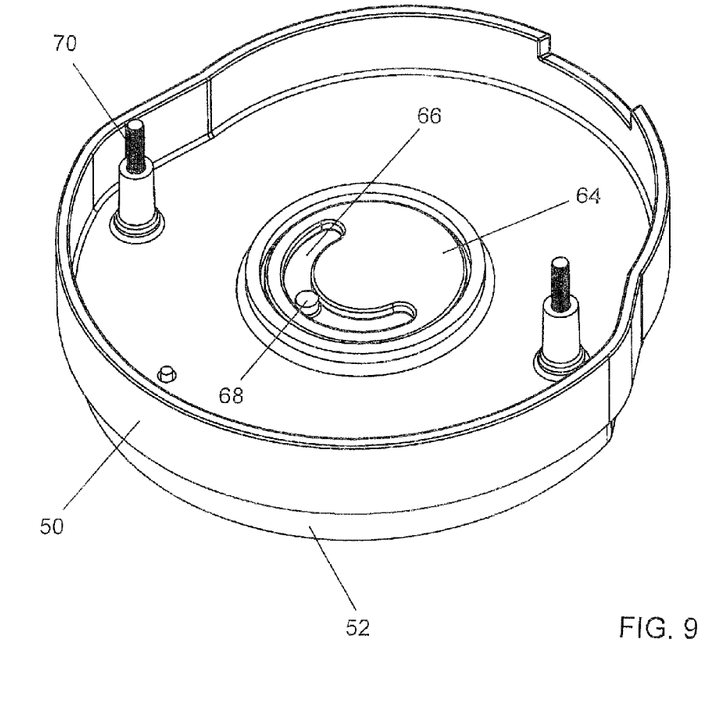
FIG. 9 is a perspective view of the middle housing of FIGS. 6 and 7.

Also shown in FIG. 6 is extension member 44 of voltage control 30 which enables electrical communication to the IC board. Further shown in FIG. 6 is wire 46 which depends from positive side of the waveform output of the IC board 34 and through opening 48 between middle housing 50 and lower housing 52 of the device. FIGS. 6 and 7 also show conductive male element 54 of electrode pad 23. The lower housing is axially journalled on screw 60 within threaded port 31 of interface element 64. Conductive coupling 56 receives the end of wire 46 furthest from IC board 34, at port 58 thereof.

Said screw 60 passes through hole 62 in the base 63 of lower housing 52 (see FIG. 7) and may rotate within threaded port 31 of mushroom-shaped piece 64 such that upper and middle housings 28 and 50 respectively may rotate in unison upon screw 60 journalled within the recess 31 within element 64. Said element 64 in combination with member 68 (see FIG. 7) limit the range of rotation of the upper and middle housings relative to lower housing to about 100 degrees or less. The slack of wire 46 is proportioned to accommodate such rotation without pulling wire 46 out of port 58 or causing tension at hole 48 in the opening 48 of middle housing 50. See FIGS. 6 to 9. Posts 70 assure a proper vertical separation between the respective housings.

It is noted that sidewalls 72 of the lower housing are slidably inserted and press-swivel rotatable within sidewalls 74 of middle housing 50. See FIGS. 7 and 8.

Figure 10:
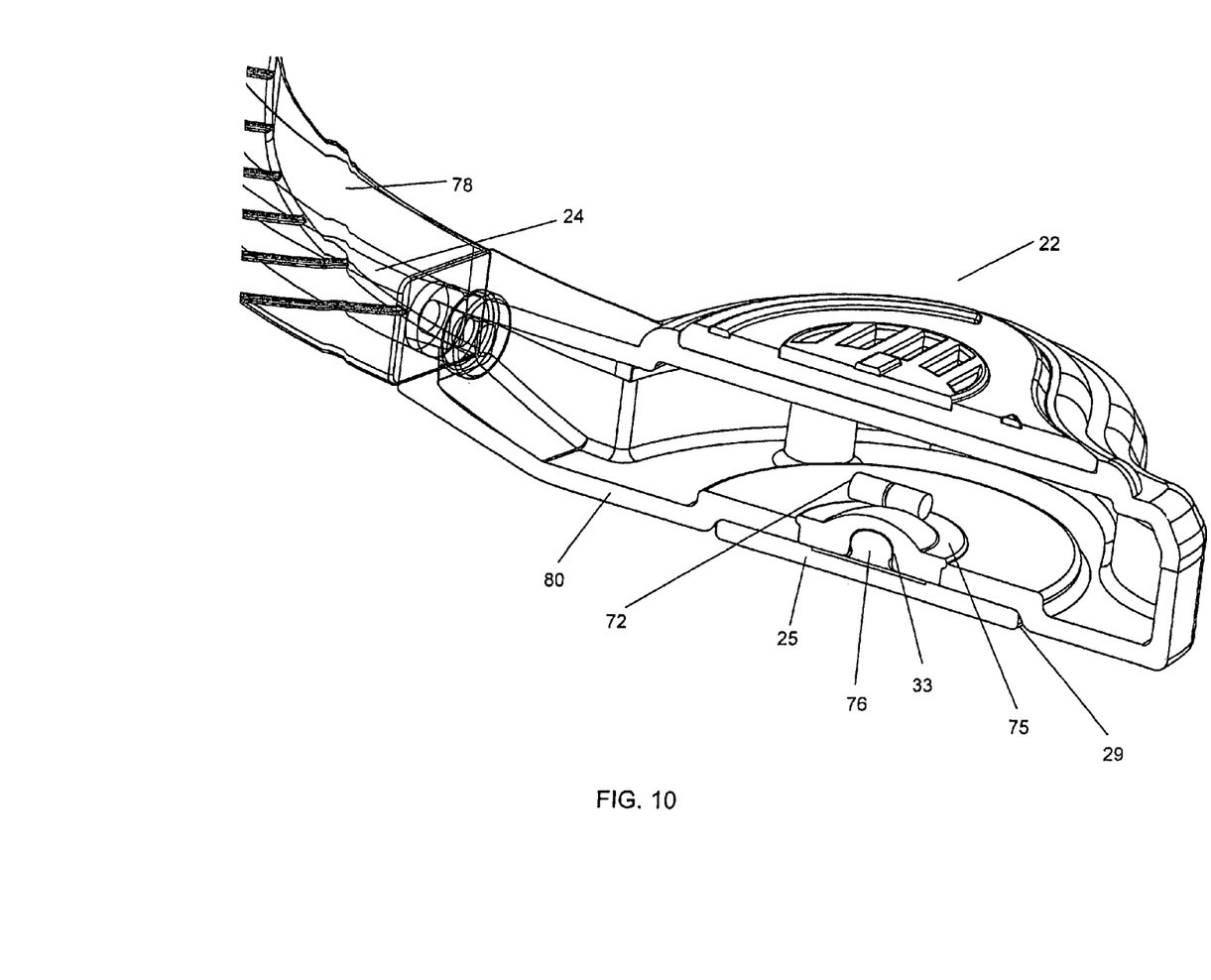
FIG. 10 is a cross-sectional view showing the parts of the negative electrode assembly, taken along Line 10-10 of FIG. 1.

In FIG. 10 is shown a break-away view of negative assembly 22 in which may also be seen cable 24 within a flexible housing 78. The end of the cable (not shown) connects to conductive port 73 and electrically communicates with coupling 75 which receives the male connector 76 of negative treatment pad 25. Negative electrode assembly 22, like the positive assembly 20, thus is provided with a conductive pad that fits within a recess (29) within the lower surface 80 of its assembly 22. It is noted that the negative assembly may rotate relative to the positive assembly upon the axle of screw 60 (see FIGS. 5-7) but the positive assembly cannot rotate about the negative assembly. That is, by reason of interface element 64, negative assembly 22 is able to rotate up to about 100 degrees about positive assembly 20, but positive assembly can only rotatable on it own axis which is defined by screw 60.

Figure 11:
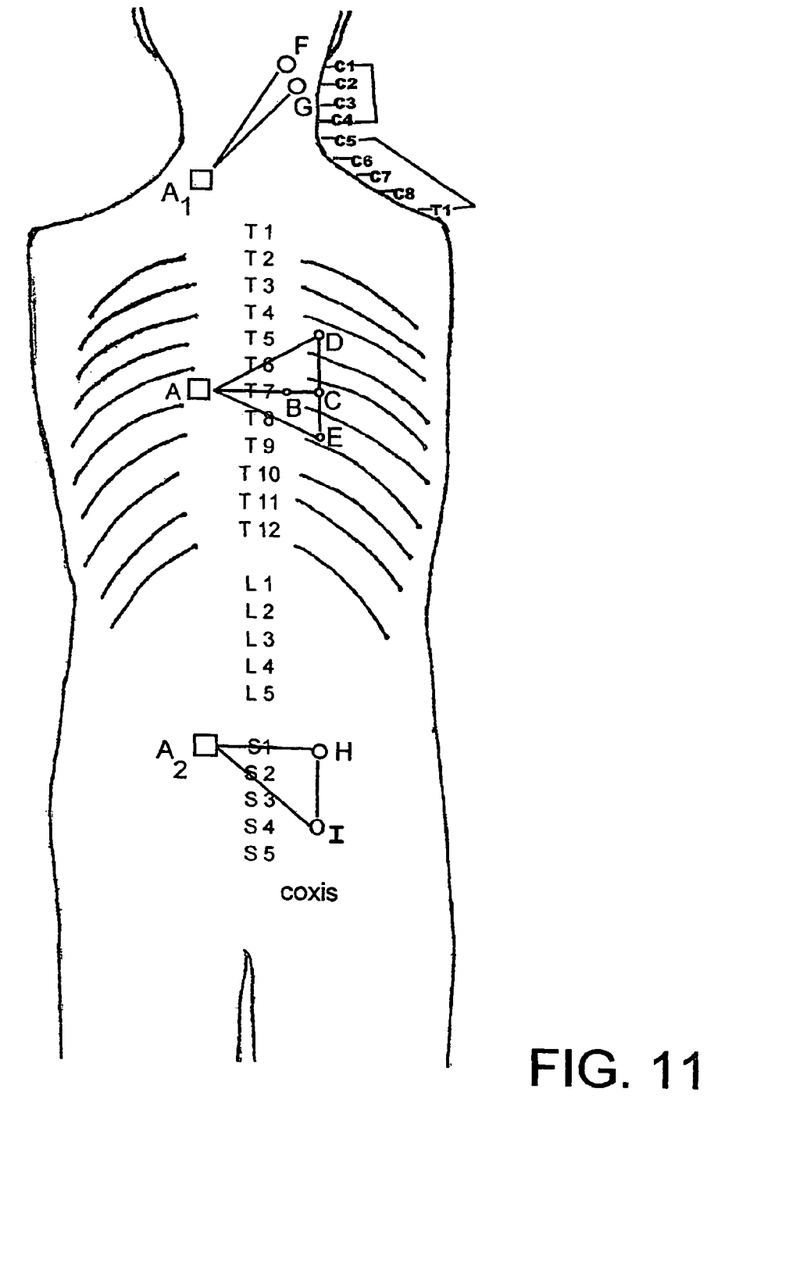
FIG. 11 is a neurological schema of the back showing areas of application of electrodes of the present apparatus.

In FIG. 11 are shown locations at which the electromagnetic physiologic waveform applicator is applied to the human body. Therein, each of the locations indicated at A, A1 and A2 represent locations of positive assembly 20, while the locations indicated by the letters D thru A, F, C, H and I are all locations at which the negative assembly 22 are selectably placed, all in the manner set forth in our parent application Ser. No. 13/663,658, referenced above. Actual contact with the skin occurs via anode pad 23 and cathode pad 25. As in noted in said parent application, one-half of the treatment by the respective anodes and cathodes occurs in the manner shown in FIG. 11, whereas in a second phase thereof, the locations of the anode are respectively reversed such that anodes therein are used at the right side of the body and all cathodes are used at the left side. The duration of the on and off periods of the waveform are controlled by a microprocessor in the IC board 34.

While there has been shown and described above the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the Claims appended herewith.

The invention claimed is:

1. An apparatus for the electro-physiologic stimulation of the human nervous system, the apparatus comprising:
   (a) a positive electrical assembly comprising;
      (i) an integrated circuit (IC) board or chip producing a sequence of physiologically compatible and acceptable electromagnetic waveforms, the IC board having respective outputs of ungrounded positive and negative sides of said waveforms;
      (ii) a battery in electrical communication with said IC board;
      (iii) a positive electrode treatment pad in electrical communication with said positive output of said waveforms, and securable within a complementary bottom of a lower housing;
      (iv) an upper housing in which said IC board is secured; and
      (v) a middle housing in axial rotational communication with said upper housing in which at least 90 degrees of rotation of the middle housing relative to said lower housing is enabled, said middle housing mechanically secured to said upper housing of the positive assembly;
   (b) a cable having one end in electrical communication with said outputs of each side of said waveforms of said IC board;
   (c) a negative electrical assembly comprising:
      (i) a channel of a housing for receiving an opposite end of said cable, carrying said output of negative waveforms;
      (ii) a negative electrode treatment pad in selectable electrical communication with a bottom of said housing of said negative assembly; and
      (iii) an electrical coupling joining said end of said cable in said channel to said negative electrode treatment pad.

2. The apparatus as recited in claim 1, in which a positive side of said IC board defines a direct electrical connection to said positive electrode treatment pad.

3. The apparatus as recited in claim 2, in which a potentiometer is provided on said upper housing of said positive assembly to control a voltage amplitude of said waveform outputs of said IC board.

4. The apparatus as recited in claim 1, in which upper surfaces of said housings include air vents.

5. The apparatus as recited in claim 4, in which said cable includes a housing provided with air vents.

6. The apparatus as recited in claim 5, in which said housing of said cable comprises a flexible housing thereabout.

7. The apparatus as recited in claim 4, comprises:
   a control for said potentiometer axially centered at a top of said upper housing of said positive electrode assembly.

8. The apparatus as recited in claim 7, further comprising:
   an IC board on-off switch provided within said control for said potentiometer.

9. The apparatus as recited in claim 1, in which said IC board includes a microprocessor that defines durations of said waveforms.

10. The apparatus as recited in claim 1, in which an extent of rotation of said upper and middle housings relative to said lower housing is defined by a rotation limiting channel within an interface element secured between said middle and lower housings and an axial rotational screw of said lower housing journalled within a bottom of said interface element.

11. The apparatus as recited in claim 10, further comprising:
   a bearing element included within securing means about said cable from the IC board between walls of said upper and middle housings, enclosing and securing an end of a wire from said cable between said housings.

* * * * *